United States Patent [19]

Kurane et al.

[11] 4,133,752

[45] Jan. 9, 1979

[54] METHOD FOR DECOMPOSITION OF PHTHALIC ACID ESTERS BY USE OF MICROORGANISMS

[75] Inventors: Ryuichiro Kurane; Tomoo Suzuki; Yoshimasa Takahara, all of Chiba, Japan

[73] Assignee: Agency of Industrial Science & Technology, Tokyo, Japan

[21] Appl. No.: 783,283

[22] Filed: Mar. 31, 1977

[30] Foreign Application Priority Data

Jun. 2, 1976 [JP] Japan .................................. 51-64985

[51] Int. Cl.² ............................ C02C 1/06; C12B 1/00
[52] U.S. Cl. ....................................... 210/12; 210/2; 195/3 R
[58] Field of Search ................ 210/2, 11, 12; 195/3 R

[56] References Cited

U.S. PATENT DOCUMENTS

| 3,871,956 | 3/1975 | Azarowics | 210/11 |
| 3,919,045 | 11/1975 | Krauch et al. | 195/3 R |
| 3,926,796 | 12/1975 | Fujita et al. | 210/11 |

OTHER PUBLICATIONS

Sakaue et al., "Microbial Decomposition of Diheptyl Phthalate," Abstract of Lecture, 1975, General Meeting of Japan Agricultural Chemical Society.

*Primary Examiner*—Thomas G. Wyse
*Attorney, Agent, or Firm*—Oblon, Fisher, Spivak, McClelland & Maier

[57] ABSTRACT

Microorganisms of a species selected from the group consisting of the specific species belonging to genus Nocardia, genus Pseudomonas, genus Brevibacterium and genus Corynebacterium, when cultured in a culture medium containing a phthalic acid ester as a carbon source, assimilate the phthalic acid ester and decompose it into carbon dioxide gas and water.

15 Claims, 3 Drawing Figures

METHOD FOR DECOMPOSITION OF PHTHALIC ACID ESTERS BY USE OF MICROORGANISMS

BACKGROUND OF THE INVENTION

This invention relates to decomposition of phthalic acid esters by use of microorganisms. Phthalic acid esters are used chiefly as plasticizers in plastic products. Gradually these phthalic acid esters dissolve out of plastic products and mingle into water, air and other similar natural elements. Since phthalic acid esters generally are sparingly soluble in water, the phthalic acid esters which dissolve out little by little into nature continue to accumulate in nature. In recent years, as a result of the sharp increase in the production of plastic products, pollution of the environment by such accumulating phthalic acid esters has risen rapidly to the extent of arresting public attention, posing a grave social issue equivalent to that once encountered with PCB.

Decomposition of phthalic acid esters by microorganisms of certain species belonging to genus Bacillus has been reported (Collection of Abstracts of Lectures at the 1975 General Meeting of Japan Agricultural Chemical Society, page 43 (1974). The method introduced in this report effectively converts diheptyl phthalates into corresponding monoheptyl phthalates. However, phthalic acid esters such as di-2-ethylhexyl phthalate, dibutyl- benzyl phthalate and dibutyl phthalate which are major plasticizers used in plastic products are not decomposed at all by this method.

An object of this invention is to provide a method which permits easy decomposition of all the phthalic acid esters into water and carbon dioxide gas.

SUMMARY OF THE INVENTION:

To accomplish the object described above according to this invention, there is provided a method for the decomposition of phthalic acid esters which comprises culturing in a culture medium containing a phthalic acid ester as a carbon source, microorganisms of at least one species selected from the group consisting of the species belonging to genus Nocardia, genus Pseudomonas, genus Brevibacterium and genus Corynebacterium or microbial flora containing said microorganisms.

The microorganisms, thus cultured in the medium containing a phthalic acid ester as a carbon source, assimilate the phthalic acid ester and decompose it into carbon dioxide gas and water.

The method of this invention is economical, because it uses microorganisms as described above. Besides, it has no possibility of entailing any secondary environmental pollution because the phthalic acid ester is decomposed into carbon dioxide gas and water.

The other objects and characteristic features of the present invention will become apparent from the description to be given in further detail herein below with reference to the accompanying drawing.

DESCRIPTION OF THE PREFERRED EMBODIMENTS

The inventors, on the belief that use of microorganisms would constitute effective means for economical and efficient decomposition of phthalic acid esters, made an extensive search for microorganic strains in nature which are capable of powerfully decomposing phthalic acid esters. They have, consequently, made a discovery that microorganisms of specific species belonging to genus Nocardia, genus Pseudomonas, genus Brevibacterium and genus Corynebacterium are capable of powerfully decomposing phthalic acid esters into water and carbon dioxide gas. The present invention has been accomplished on the basis of this discovery.

To be more specific, microorganisms of a species selected from the specific species belonging to genus Nocardia, genus Pseudomonas, genus Brevibacterium and genus Corynebacterium, when cultured in a culture medium containing phthalic acid esters as a carbon source, advantageously assimilate the phthalic acid esters.

Figure 1:
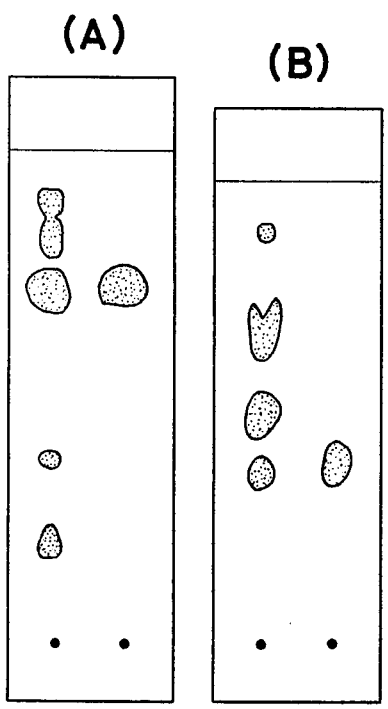
FIG. 1 represents thin-layer chromatographs taken of acidic ether extracts from microorganic culture broths.

The path through which the decomposition of phthalic acid esters by said microorganisms occurs will be described in detail. First, the microorganisms are inoculated to a culture medium containing a phthalic acid ester. When the organic carbon content in the culture medium reaches the maximum level (in about 30 hours), the culture broth is extracted with ether and the ether extract is dissolved in an alcoholic solvent. The resultant solution is subjected to thin-layer chromatography (using a silica gel plate) and phthalic acid is similarly chromatographed, and the results are compared with each other. As indicated in FIG. 1, the Rf value obtained of the ether extract and the Rf value obtained of phthalic acid are equal to each other, no matter whether there is used a solvent composed of 4 parts of normal butanol, 1 part of formic acid and 2 parts of water (FIG. 1(A)) or a solvent composed of 100 parts of 96% ethanol, 12 parts of water and 16 parts of 25% ammonia (FIG. 1(B)). The agreement of the two Rf values is a proof that the ether extract contains phthalic acid, namely that part of the phthalic acid ester in the culture medium has been converted into phthalic acid.

Then, after about 40 hours of culture, the culture broth is again extracted with ether. The extract is dissolved in a solvent composed of 4 parts of normal butanol, 1 part of formic acid and 2 parts of water and the resultant solution is subjected to thin-layer chromatography. Protocatechuic acid is similarly chromatographed. The results thus obtained are shown in Table 1 below.

Table 1

|  | Rf values of thin-layer chromatography | |
|---|---|---|
|  | BCG color development | UV color development |
| Ether extract | 0.84 | 0.84 |
| Protocatechuic acid | 0.85 | 0.85 |

The close approximation between the value of BCG color development with the ether extract and that with the protocatechuate implies that the ether extract has an acidic carboxyl group at a spot identical with the spot of the acidic carboxyl group of the protocatechuate. Further, the close approximation between the value of UV color development with the ether extract and that with the protocatechuate implies that the ether extract has the same benzene ring as the protocatechuic acid. These approximations of said values provide a proof that after 40 hours of culture, the culture broth contains protocatechuic acid, namely that said phthalic acid has been further decomposed into protocatechuic acid.

When the culture medium is analyzed at intervals along the course of the culture with respect to the change of the total organic carbon content in the culture medium and the residual rate of phthalic acid ester, there are obtained the results as indicated in Table 2 below.

Table 2

| Culture time (hours) | 24 | 30 | 48 | 52 |
|---|---|---|---|---|
| Total organic carbon content (ppm) | 17 | 23 | 6 | 5 |
| Residual ratio of phthalic acid ester (%) | 75 | 68 | 33 | 7 |

In the first portion of the culture time, the total organic carbon content increases in proportion as the culture time increases. This is because the phthalic acid ester contained in the medium is decomposed into phthalic acid and protocatechuic acid. When the culture time adds up to about 48 hours, the carbon content in the metabolic intermediate of decomposition sharply decreases, with the result that the culture broth contains practically no carbon. This fact, when considered in conjunction with the observation that, as indicated in Table 4 afterward, both phthalic acid and protocatechuic acid are assimilable by the microorganisms of the present invention, it is a logical conclusion that the phthalic acid ester is completely decomposed into carbon dioxide gas and water.

As indicated by the following formula, the microorganisms discharge a phthalate-decomposing enzyme which severs the phthalic acid ester at the ester position and converts the ester into phthalic acid and further into protocatechuic acid, thereafter induces ring clevage in the benzene ring and finally brings the decomposition to the extent of thorough conversion into carbon dioxide gas and water.

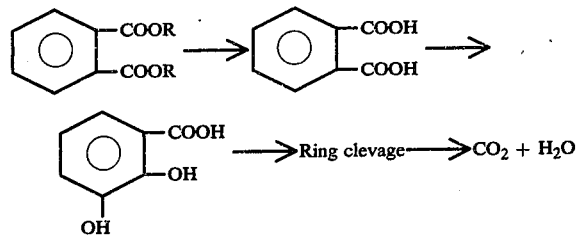

Assimilability of the pendant portions of the phthalic acid esters has also been studied. The study has led to a revelation that the microorganisms assimilate phthalic acid esters well irrespectively of the question as to whether the pendant portions thereof are of the normal type, branched type (iso or 2-ethyl type), glycol type, oxy type, benzene ring type or double bond type. The microorganisms of the indicated species are capable of assimilating the pendant portions at the para- position as well as those at the ortho position. Thus, phthalic acid, iso-phthalic acid, terephthalic acid, hexahydro-phthalic acid, protocatechuic acids and the like are invariably assimilated advantageously.

The present invention which is directed to the decomposition of phthalic acid esters by use of specific microorganisms, therefore, can be applied to a wide spectrum of uses.

The mycological characteristics of the species of microorganisms to be used for the purpose of this invention will be indicated in Table 3. The species of microorganisms given in the table, through reference of their respective mycological properties to the "Bergy's Manual, 8th ed," are identified as those belonging to genus Nocardia, genus Corynebacterium, genus Brevibacterium and genus Pseudomonas.

With reference to the contents of Table 3, *Nocardia erythropolis* KR-S-1, Corynebacterium KR-240-1, Brevibacterium KR-240-4 and Pseudomonas KR-256-1 were deposited on April 19, 1976 at the Fermentation Research Institute, Agency of Industrial Science and Technology in Chiba City of Japan, under the respectively assigned deposit numbers of FERM No. 3530 FERM No. 3527, FERM No. 3528 and FERM No. 3529. *Nocardia restricta* KR-242-1, *Nocardia blackwellii* KR-254-1, *Nocardia erythropolis* KR-256-2, *Nocardia restricta* KR-260-1, *Nocardia erythropolis* KR-23-1, *Nocardia erythropolis* KR-23-3, *Nocardia minima* KR-48-1, *Nocardia calcarea* KR-62-1, *Nocardia erythropolis* KR-71-1, *Corynebacterium pseudophthalicas* KR-242-2, *Brevibacterium pseudolinens* KR-62-3 and *Pseudomonas multivorans* KR-254-4 were deposited on February 9, 1977 at the same depository, under the respectively assigned deposit numbers FERM No. 3919, FERM No. 3921, FERM No. 3923, FERM No. 3924, FERM No. 3913, FERM No. 3914, FERM No. 3915, FERM No. 3916, FERM No. 3918, FERM No. 3920, FERM No. 3917 and FERM No. 3922.

The cultures of the microorganisms mentioned above are to be made readily available to the public upon grant of patent in accordance with an agreement between the depository and the depositor, the conditions of the agreement being such that the culture will be maintained during the pendency of the application and that all restrictions on the availability to the public of the culture will be irrevokably removed upon granting of the patent.

Table 3

| Genus | | Nocardia | | | | | | | | | | | Corynebacterium | | Brevibacterium | | Pseudomonas | |
|---|---|---|---|---|---|---|---|---|---|---|---|---|---|---|---|---|---|---|
| Characteristics \ FERM No. | 3530 | 3919 | 3921 | 3923 | 3924 | 3913 | 3914 | 3915 | 3916 | 3918 | 3527 | 3920 | 3528 | 3917 | 3529 | 3922 |
| Gram-stain | + | + | + | + | + | + | + | + | + | + | + | + | + | + | − | − |
| Motility | − | − | − | − | − | − | − | − | − | − | − | − | − | − | + | + |
| Colony Nutrient agar Color | pinkish-cream | " | " | " | " | " | " | " | " | " | carotenoid | " | carotenoid | " | gray-cream | Yellow |
| Gloss | glistening | " | " | " | " | " | " | " | " | " | glistenless | " | glistenless | " | glistening | " |
| Shape | smooth circular | " | " | " | " | " | " | " | " | " | smooth circular | " | dry/rough | " | smooth circular | " |
| R-medium (3) | " | " | " | " | " | " | " | " | " | " | " | " | " | " | " | " |
| P-medium (4) | " | " | " | " | " | " | " | " | " | " | " | " | " | " | " | " |
| Flagella | none | none | none | none | none | none | none | none | none | none | none | none | none | none | polar flagella | polar flagella |
| Amino acid in cell wall Meso-diamino pimelic acid | + | + | + | + | + | + | + | + | + | + | + | + | + | + | | |
| LL-diamino pimelic acid | − | − | − | − | − | − | − | − | − | − | − | − | − | − | | |
| Type of cell division | fragmentation | " | " | " | " | " | " | " | " | " | snapping | snapping | bending | bending | | |
| Aerobic growth | + | + | + | + | + | + | + | + | + | + | + | + | + | + | + | + |
| Catalase | + | + | + | + | + | + | + | + | + | + | + | + | + | + | + | + |
| Oxidase | − | − | − | − | − | − | − | − | − | − | − | − | − | − | − | − |
| DNase | + | + | + | + | + | + | + | + | + | + | ± | ± | ± | + | | |
| Urease | ++ | ++ | ++ | ++ | ++ | ++ | ++ | ++ | ++ | ++ | ± | ± | ± | ± | | |
| Cellulase | − | − | − | − | − | − | − | − | − | − | − | − | − | − | | |
| O-F test | O | O | O | O | O | O | O | O | O | O | F | F | F | F | O | O |
| Hydrolysis of gelatin | − | − | − | − | − | − | − | − | − | − | − | − | − | − | − | − |
| Nitrate reduction | ++ | ++ | ++ | ++ | ++ | ++ | ++ | ++ | ++ | ++ | ++ | ++ | ++ | ++ | ++ | ++ |
| Nitrate medium | − | + | ± | ± | − | − | − | − | − | − | + | + | + | + | + | + |
| Succinate-nitrate medium | + | + | + | − | − | − | − | − | − | − | − | − | − | − | − | − |
| Nitrate respiration | + | + | + | + | + | + | + | + | + | + | + | + | + | + | + | + |
| Acid-fast | − | − | − | − | − | − | − | − | − | − | − | − | − | − | − | − |
| Litmus-milk | alkali | " | " | " | " | " | " | " | " | " | alkali | " | alkali | " | alkali | unchanged |
| Lysozyme resistant | + | + | + | + | + | + | + | + | + | + | + | + | + | + | + | + |
| Decomposition of casein | − | − | − | − | − | − | − | − | − | − | − | − | − | − | + | + |
| Decomposition of dextrin | + | + | + | + | + | + | + | + | + | + | + | + | + | + | + | ± |
| Assimilation of n-hexadecane | +++++ | +++++ | +++ | ++++++ | ++++ | +++++ | +++++ | +++++ | +++++ | +++++ | +++++ | +++++ | +++++ | +++++ | +++++ | +++++ |
| Assimilation of organic acid | | | | | | | | | | | | | | | | |
| Acetate | − | − | − | − | − | − | − | − | − | − | − | − | − | − | − | − |
| Citrate | − | − | − | − | − | − | − | − | − | − | − | − | − | − | − | − |
| Formate | + | ++ | ++ | + | + | + | + | ++ | ++ | + | − | − | − | − | ± | ± |
| Lactate | − | − | − | − | − | − | − | − | − | − | − | − | − | − | ± | ± |
| Oxaloacetate | + | − | − | + | − | − | − | − | − | − | − | − | − | − | − | − |
| Succinate | − | − | − | − | − | − | − | − | − | − | − | − | − | − | − | − |
| Acid from sugar | | | | | | | | | | | | | | | | |
| D-arabinose | − | − | − | − | − | − | − | − | − | − | − | − | − | − | − | − |
| Erythritol | − | − | − | − | − | − | − | − | − | − | − | − | − | − | − | − |
| D-fructose | − | − | − | − | − | − | − | − | − | − | − | − | − | − | − | − |
| D-galactose | − | − | − | − | − | − | − | − | − | − | − | − | − | − | − | − |
| Glucose | − | − | − | − | − | − | − | − | − | − | − | − | − | − | − | − |
| Inositol | − | − | − | − | − | − | − | − | − | − | − | − | − | − | − | − |
| Lactose | − | − | − | − | − | − | − | − | − | − | − | − | − | − | − | − |
| Mannitol | − | − | − | − | − | − | − | − | − | − | − | − | − | − | − | − |
| Raffinose | − | − | − | − | − | − | − | − | − | − | − | − | − | − | − | − |
| L-rhamnose | − | − | − | − | − | − | − | − | − | − | − | − | − | − | − | − |
| L-sorbose | − | − | − | − | − | − | − | − | − | − | − | − | − | − | − | − |
| Sucrose | − | − | − | − | − | − | − | − | − | − | − | − | − | − | − | − |
| Trehalose | − | − | − | − | − | − | − | − | − | − | − | − | − | − | − | − |
| D-xylose | − | − | − | − | − | − | − | − | − | − | − | − | − | − | − | − |

The species of microorganisms described above may be cultured on an individual basis. They may otherwise be cultured in the form of mixtures of two or more species. Similarly advantageous results of decomposition can be obtained by culturing microorganic flora including such species of microorganisms. Effective use of the microbial flora may be attained by subjecting activated sludge containing microorganisms of this invention in advance to a taming culture in a culture medium containing a phthalic acid ester and thereby permitting growth of said microorganisms and putting the activated sludge to service. It may otherwise be accomplished by adding microorganisms to activated sludge and then adding the resultant activated sludge to a substance containing a phthalic acid ester desired to be decomposed. Alternatively, it may be materialized by adding microorganisms and activated sludge separately to the substance.

Use of microorganisms of the species of this invention permits conversion of the phthalic acid ester, through decomposition of the ester linkage thereof, into phthalic acid and further into protocatechuic acid and thereafter brings about cleavage of the benzene ring. Besides, the microorganisms can decompose the pendant position of normal type, iso type, 2-ethyl type, glycol type, oxy type, benzene ring type, double bond type, para-position bond type or any other type as shown in Table 4.

In the Table 4, "DEP" is an abbreviation of di-ethyl phthalate, "DnPP" di-normal-propyl phthalate, "DnBP" dinormal-butyl phthalate, "DnAMP" di-normal-amyl phthalate, "DHP" di-heptyl phthalate, "DnOP" di-normal-octyl phthalate, "DNP" di-nonyl phthalate, "DDP" di-dodecyl phthalate, "DTDP" di-tridecyl phthalate, "DIPP" di-isopropyl phthalate "DIBP" di-isobutyl phthalate, "DIDP" di-isodecyl phthalate, "DEHP" di-2-ethylhexyl phthalate, "DEHHP" di-2-ethylhexylhexahydro phthalate, "MPEG" methyl phthalylethylglycolate, "EPEG" ethylphthalylethylglycolate, "BPBG" butylphthalylbutylglycolate, "DMEP" di-2-mesoxalethyl phthalate, "DBEP" di-2-butoxylethyl phthalate, "BBP" di-butyl-benzyl phthalate, "DPeP" di-phenyl phthalate, "DCHP" di-cyclohexyl phthalate, "DALP" di-allyl phthalate and "DETP" di-ethylterephthalate.

Table 4

| Genus | Nocardia | | | | | | | | | | Corynebacterium | | Brevibacterium | Pseudomonas | |
|---|---|---|---|---|---|---|---|---|---|---|---|---|---|---|---|
| FERM No. | 3530 | 3919 | 3921 | 3923 | 3924 | 3913 | 3914 | 3915 | 3916 | 3918 | 3527 | 3920 | 3528 | 3917 | 3529 | 3922 |

Phthalic acid ester:

(Normal type)
- DEP
- DnPP
- DnBP
- DnAMP
- DHP
- DnOP
- DNP
- DDP
- DTDP (Iso type)
- DIPP
- DIBP
- DIDP (2-ethyl type)
- DEHP
- DEHHP (Glycol type)
- MPEG
- EPEG
- BPBG (Oxy type)
- DMEP
- DBEP (Benzene type)
- BBP
- DPeP
- DCHP (Double bond type)
- DALP (Para-position bond type)
- DETP Phthalic acid
Iso-phthalic acid
Tere-phthalic acid
Hexahydro-phthalic acid
Protocatechuic acid For efficient decomposition of a phthalic acid ester by these decomposing microorganisms, it is desirable that the phthalic acid ester be dispersed as finely as possible to increase the interface area of contact with the decomposing microorganisms. As concerns the state of said dispersion, the ester may be dispersed in the form of fine fibers, thin films or finely divided particles. Otherwise, the phthalic acid ester may be dissolved such as in an organic solvent and thereafter suspended in water and it may be dispersed with the aid of a surface active agent (such as, for example, Tween 80). During the decomposition, the temperature of the reaction system is desired to be maintained in the range of from 5 to 40° C., preferably from 20 to 30° C. and the pH value thereof in the range of from 3 to 10, preferably from 4 to 9. The reaction of decomposition proceeds in a liquid phase or even in a solid phase insofar as there is sufficient supply of water. Feeding of air to the reaction system serves to accelerate the reaction. Additional incorporation of nutrient sources such as vitamins is effective in enhancing the reaction of decomposition.

A culture medium which is useful for the culture of the microorganisms of this invention is made up of substance containing inorganic nitrogen sources such as nitrates, ammonium salts and ammonium sulfate, organic nitrogen sources such as soybean flour and meat extract, carbon sources such as starch and glucose and inorganic salts such as sodium chloride, potassium chloride, magnesium sulfate, calcium carbonate, iron sulfate and manganese sulfate. This means that night soil, animal wastes, wastes from farm products, wastes from food processing industries, spent fermentation broths and residues, microorganic cells discharged from fermentation plants and town garbage can be effectively used as media for the culture. Desired assimilation of a phthalic acid ester contained in a given substance, therefore, can be accomplished by adding the substance to any of the wastes mentioned above, inoculating the microorganisms to the culture medium and maintaining the medium under the culture conditions described above. Since the phthalic acid ester can serve by itself as a carbon source, incorporation of some other carbon source to the culture medium may be omitted.

Although the advantageous phthalic acid ester content in the medium is variable with the particular species of the microorganisms inoculated to the medium, the composition of the medium and the reaction conditions involved, effective decomposition of the phthalic acid ester is obtained when the content is not more than 2%. The reaction time is generally in the range of from 20 to 150 hours, though it is variable to some extent with the reaction conditions involved. As for the size of inoculation (added microorganic activity), one loop full of the seed culture will suffice. The microorganisms introduced in this amount, when cultured in the medium, gradually attain growth and gain in activity enough to provide required decomposition of the phthalic acid ester.

The decomposition of phthalic acid esters by the method of this invention relies entirely upon assimilation by microorganisms as described above and, therefore, can be accomplished economically. Since this method decomposes all the phthalic acid esters into carbon dioxide and water, i.e. substances which are both perfectly free from all forms of environmental pollution, the decomposition by this invention has absolutely no possibility of entailing any secondary pollution. The decomposition as a reaction involved in this case involves no particularly difficult conditions, the phthalic acid ester entrained by the effluent from a plastic plant or by the raw water fed to the water purification station for a municipal water system can be effectively decomposed by subjecting the plant effluent to the treatment by the method of this invention en route to the nearby body of water or by similarly treating the raw water en route to the purification station, thus successfully preventing the phthalic acid ester from causing water pollution or from entering the human system. Since night soil or town garbage can be used as a culture medium for the microorganic decomposition of the phthalic acid ester, the method of this invention fulfils an additional purpose of disposing of such troublesome waste. The animal experiment conducted by the inventors has revealed that the microorganisms of this invention injected into or orally taken into animals cause no adverse effect on the systems of the animals. This suggests a possibility that in the future, the microorganisms will become applicable to decomposition of phthalic acid esters accumulated in the human system.

The present invention will be described more specifically below with reference to working examples. The amounts of phthalic acid esters indicated in these examples are those determined by the following procedure:

Procedure for determination of phthalic acid ester:

All the phthalic acid esters were invariably determined by analysis using gas chromatography (FID). The determination of di-2-ethylhexyl phthalate (DEHP), for example, was made by using a column of Silicon OV-17 (2 m in length), a column temperature of 270° C., an injection temperature of 300° C., a carrier gas of nitrogen and a fixed amount of anthrone as an internal standard substance.

Culture broths were tested for growth of microorganisms by adding an ethanol/n-butanol/chloroform (10:10:1) type solvent to the culture broths to rid them of turbidity due to phthalic acid esters and measuring their absorbancy at 660 nm.

EXAMPLE 1

A 500-ml Erlenmeyer flask was charged with 150 ml of a culture medium (pH 7) composed of 1% (10,000 ppm) of DEHP, 0.1% of ammonium sulfate, 0.02% of potassium phosphate I, 0.16% of potassium phosphate II, 0.02% of magnesium sulfate, 0.01% of calcium chloride, 0.01% of sodium chloride, 0.001% of iron sulfate, 0.0005% of sodium molybdate, 0.0005% of manganese sulfate, 0.0005% of sodium tungstate, 0.0004% of calcium pantothenate, 0.002% of inositol, 0.0004% of nicotine, 0.0002% of P-aminobenzoic acid, 0.0004% of pyridoxine hydrochloride, 0.0004% of thiamine hydrochloride, 0.0004% of riboflavin, 0.000002% of biotin, 0.0000005% of $VB_{12}$ and the balance of water. To this liquid culture medium (DEHP culture medium), one platinum loop full of the cells of Pseudomonas KR-256-1 (FERM No. 3529) pre-cultured for two days (30° C.) on a slant DEHP agar culture medium of the same composition (the preceding DEHP culture medium plus 1.5% of agar) was inoculated. The microorganisms were subjected to shaken culture by rotation at 30° C. After 100 hours of the shaken culture, a 3-ml sample was taken. Of the sample, a 2-ml portion was assayed for phthalic acid ester and the remaining 1-ml portion was tested for growth of microorganisms.

It was consequently found that the microorganisms decomposed about 98% of the DEHP present and they were multiplied to about 500 times the original size.

EXAMPLE 2

To the same DEHP culture medium as indicated in Example 1, one platinum loop full of the cells of *Nocardia erythropolis* KR-S-1 (FERM No. 3530) pre-cultured by the same method under the same conditions as those of Example 1 was inoculated similarly to Example 1. In the same way as in Example 1, the culture broth was sampled after 100 hours of shaken culture.

It was found that the microorganisms decomposed about 98% of DEHP present.

EXAMPLE 3

The procedure of Example 1 was repeated with respect to Corynebacterium KR-240-1 (FERM No. 3527) by using the same DEHP culture medium and performing the shaken culture in the same manner under the same conditions as those of Example 1.

It was found that over 100 hours of the shaken culture, the microorganisms decomposed about 30% of DEHP.

EXAMPLE 4

The procedure of Example 1 was repeated with respect to Brevibacterium KR-240-4 (FERM No. 3528) by using the same DEHP culture medium and performing the shaken culture in the same manner under the same conditions as those of Example 1.

It was consequently found over after 100 hours of the shaken culture, the microorganisms decomposed about 35% of DEHP present.

EXAMPLE 5

In aliquots of ordinary activated sludge (MLSS (suspended substance): 4,000–6,000 ppm) cultured in synthesized sewage water, the microorganisms of the species pre-cultured on slanted DEHP agar culture media as in Examples 1–4 respectively were placed, each in the amount of one platinum loop full. The resultant mixtures were each added to substances containing 0.1% of DEHP. The results are as shown in Table 5.

Table 5

|  | Decomposition ratio (%) | | |
| --- | --- | --- | --- |
|  | 24(hours) | 72(hours) | 144(hours) |
| Activated sludge + | | | |
| (1) *Nocardia erythropolis* KR-S-1 | 90 | 100 | 100 |
| (2) Pseudomonas KR-256-1 | 70 | 95 | 100 |
| (3) Corynebacterium KR-240-1 | 25 | 40 | 50 |
| (4) Brevibacterium KR-240-4 | 30 | 40 | 55 |
| Activated sludge + (1), (2), (3) & (4) | 78 | 91 | 100 |
| Activated sludge | 2 | 9 | 20 |

It is evident from Table 5 that the decomposition of DEHP is obtained far more efficiently in the presence of the microorganisms than in their absence.

EXAMPLE 6

Figure 2:
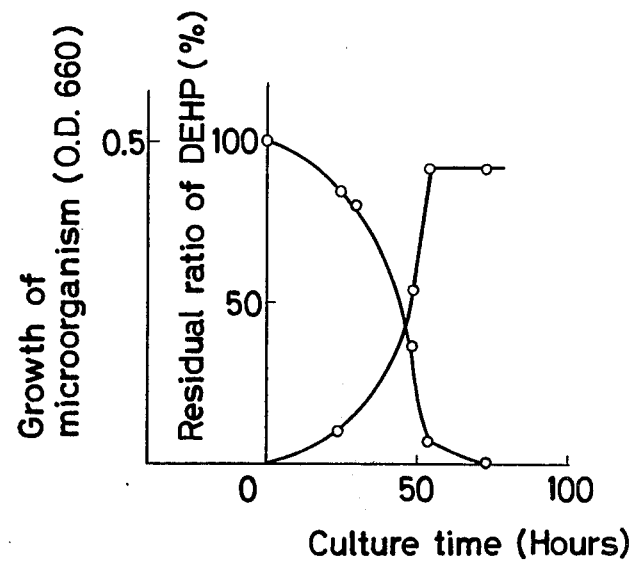
FIG. 2 is a graph showing the relation between the ratio of decomposition of phthalic acid esters by the microorganisms of this invention and the growth of the microorganisms.

A culture medium 150 ml, having substantially the same composition as that of the culture medium of Example 1, except the initial concentration of DEHP was 0.5%, was adjusted to pH 7. In this culture medium, one platinum loop full of the cells of Pseudomonas KR-256-1 (FERM No, 3529) inoculated thereto was cultured at a controlled temperature of 30° C. for 70 hours. The time-course change of the decomposition ratio of DEHP and the time-course change of the growth of microorganisms were as shown in FIG. 2. In FIG. 2, the curve "A" represents the residual ratio of DEHP and the curve "B" the growth of microorganisms. It is clearly seen from FIG. 2 that perfect decomposition of DEHP is obtained after elapse of about 70 hours of culture time. It is also evident from the graph that the inoculated microorganisms are rapidly multiplied to 500 times the original amount over the first 50 hours of culture time and after that the microorganisms show practically no discernible multiplication as the residue of DEHP substantially ceases to exist.

EXAMPLE 7

Figure 3:
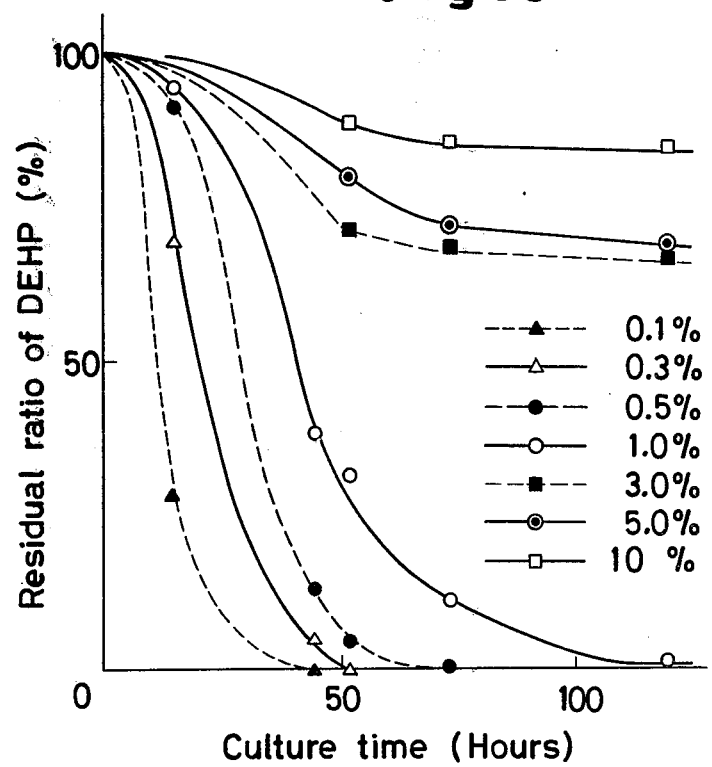
FIG. 3 is a graph showing the relation between the concentration of a phthalic acid ester and the ratio of decomposition thereof.

The microorganisms of the same species as that of Example 6 were cultured by repeating the procedure of Example 6, except the initial concentration of DEHP was varied in the range of from 0.1 to 10%. The results were as shown in FIG. 3. The data indicate that perfect decomposition of DEHP is obtained after about 50 hours of culture time where the initial DEHP concentration is 0.1% or 0.3% and after 70 hours of culture time where the initial DEHP concentration is 0.5% respectively. When the concentration is 1%, more than 95% of DEHP is decomposed over 100 hours of culture time.

By following the procedure described above, the microorganisms of Pseudomonas KR-256-1 (FERM No. 3529) was cultured for 52 hours, with the initial concentration of DEHP fixed at 0.5% and the pH value varied in the range of from 2 to 11. The results were as shown in Table 6.

Table 6

| Initial pH value | Decomposition ratio (%) |
| --- | --- |
| 2 | 3 |
| 4 | 85 |
| 6 | 95 |
| 7 | 95 |
| 9 | 80 |
| 11 | 2.5 |

It is evident from the data that advantageous decomposition of DEHP is obtained so long as the initial pH value falls in the range of from 4 to 9.

EXAMPLE 8

A composition containing 1% of DEHP was adjusted to an initial pH of 7. In aliquots of this composition, the microorganisms of the species indicated in Table 7 were cultured for 52 and 100 hours, with the temperature maintained at 30° C. The results were as shown in Table 7.

Table 7

|  | Decomposition ratio (%) | |
| --- | --- | --- |
| Species used | 52 hours | 100 hours |
| Pseudomonas KR-256-1 | 60 | 98 |
| Nocardia KR-S-1 | 80 | 99 |
| Corynebacterium KR-240-1 | 20 | 30 |
| Brevibacterium KR-240-4 | 25 | 35 |

EXAMPLE 9

Culture media having the same composition as that of the culture medium of Example 1, except a varying phthalic acid ester was contained at a concentration of 0.6%, were adjusted to pH 7 and placed, each in the amount of 150 ml, in separate Erlenmeyer flasks. Microorganisms of a varying species were inoculated, in the amount of one platinum loop full each, to the respective culture media and subjected to shaken culture at 30° C. for about 120 hours. The culture broths consequently obtained were rid of their turbidity due to phthalic acid esters by addition of the aforementioned solvent and then tested for absorbancy at 660 nm. The results were as shown in Table 3.

The degree of assimilation of phthalic acid esters was rated in accordance with the degree of absorbancy on the "− to ++++" scale, wherein "−" denotes a value not exceeding 0.001, "±" a value between 0.001 and 0.05, "+" a value between 0.05 and 0.2, "++" a value between 0.2 and 0.3, "+++" a value between 0.3 and 0.4 and "++++" a value exceeding 0.4 respectively.

It is evident from the table that all the phthalic acid esters, phthalic acid, iso-phthalic acid, tere-phthalic acid, hexahydro-phthalic acid and protocatechuic acid are invariably assimilated advantageously by the method of this invention.

What is claimed is:

1. A method for the decomposition of a phthalic acid ester comprising the step of culturing in a culture medium containing said phthalic acid ester a microorganism selected from the group consisting of *Nocardia erythropolis* KR-S-1 (FERM No. 3530), *Nocardia restricta* KR-242-1 (FERM No. 3919), *Nocardia blackwellii* KR-254-1 (FERM No. 3921), *Nocardia erythropolis* KR-256-2 (FERM No. 3923), *Nocardia restricta* KR-260-2 (FERM No. 3924), *Nocardia erythropolis* KR-23-1 (FERM No. 3913), *Nocardia erythropolis* KR-23-3 (FERM No. 3914), *Nocardia minima* KR-48-1 (FERM No. 3915), *Nocardia calcarea* KR-62-1 (FERM No. 3916), and *Nocardia erythropolis* KR-71-1 (FERM No. 3918).

2. The method for the decomposition according to claim 1, wherein the culture is made by using a culture medium containing not more than 10% of the phthalic acid ester.

3. The method for the decomposition according to claim 1, wherein the culture is made by keeping the pH value of the culture medium in the range of from 4 to 9 and the temperature thereof in the range of from 5° C. to 40° C.

4. The method for the decomposition according to claim 1, wherein the microorganisms to be used are those of a microbial flora.

5. The method of claim 1 wherein said phthalic acid ester is decomposed to carbon dioxide and water, and wherein said medium is kept at a pH of from 4 to 9 and a temperature of from 5° to 40° C.

6. The method of claim 1 wherein said microorganism is *Nocardia erythopolis* KR-S-1 (FERM No. 3530).

7. The method of claim 1 wherein said microorganism is *Nocardia restricta* KR-242-1 (FERM No. 3919).

8. The method of claim 1 wherein said microorganism is *Nocardia blackwellii* KR-254-1 (FERM No. 3921).

9. The method of claim 1 wherein said microorganism is *Nocardia erythopolis* KR-256-2 (FERM No. 3923).

10. The method of claim 1 wherein said microorganism is *Nocardia restricta* KR-260-2 (FERM No. 3924).

11. The method of claim 1 wherein said microorganism is *Nocardia erythopolis* KR-23-1 (FERM No. 3913).

12. The method of claim 1 wherein said microorganism is *Nocardia erythopolis* KR-23-3 (FERM No. 3914).

13. The method of claim 1 wherein said microorganism is *Nocardia minima* KR-481 (FERM No. 3915).

14. The method of claim 1 wherein said microorganism is *Nocardia calcarea* KR-62-1 (FERM No. 3916).

15. The method of claim 1 wherein said microorganism is *Nocardia erythopolis* KR-71-1 (FERM No. 3918).

* * * * *